(12) United States Patent
Sugiura et al.

(10) Patent No.: US 7,794,384 B2
(45) Date of Patent: Sep. 14, 2010

(54) DUAL COMMUNICATION INTERFACE FOR ARTIFICIAL HEART SYSTEM

(75) Inventors: Naoya Sugiura, Ann Arbor, MI (US); Alexander Medvedev, Ann Arbor, MI (US)

(73) Assignee: Terumo Heart, Inc., Ann Arbor, MI (US)

( * ) Notice: Subject to any disclaimer, the term of this patent is extended or adjusted under 35 U.S.C. 154(b) by 0 days.

(21) Appl. No.: 11/999,858

(22) Filed: Dec. 7, 2007

(65) Prior Publication Data
US 2009/0149951 A1 Jun. 11, 2009

(51) Int. Cl.
*A61M 1/10* (2006.01)

(52) U.S. Cl. .............. 600/16; 600/17; 607/32; 607/60; 623/3.1; 623/3.13

(58) Field of Classification Search ............. 600/16–17; 607/30–32, 60; 340/539.12; 623/3.1, 3.13
See application file for complete search history.

(56) References Cited

U.S. PATENT DOCUMENTS

| | | | |
|---|---|---|---|
| 5,309,920 A * | 5/1994 | Gallant et al. ............. | 600/523 |
| 5,342,408 A * | 8/1994 | deCoriolis et al. .......... | 607/32 |
| 6,106,551 A | 8/2000 | Crossett et al. | |
| 6,123,726 A | 9/2000 | Mori et al. | |
| 6,183,412 B1 | 2/2001 | Benkowski et al. | |
| 6,336,900 B1 * | 1/2002 | Alleckson et al. ........... | 600/485 |
| 6,409,674 B1 | 6/2002 | Brockway et al. | |
| 6,511,412 B1 | 1/2003 | Freed et al. | |
| 6,925,328 B2 | 8/2005 | Foster et al. | |
| 2002/0143372 A1 * | 10/2002 | Snell et al. ................ | 607/30 |
| 2004/0204743 A1 * | 10/2004 | McGrath et al. ........... | 607/5 |
| 2004/0260363 A1 * | 12/2004 | Arx et al. .................. | 607/60 |
| 2005/0014991 A1 | 1/2005 | Sugiura | |
| 2006/0017575 A1 * | 1/2006 | McAdams .................. | 340/573.1 |
| 2006/0149339 A1 * | 7/2006 | Burnes et al. .............. | 607/60 |
| 2007/0123946 A1 * | 5/2007 | Masoud ..................... | 607/32 |
| 2007/0197854 A1 * | 8/2007 | Marseille et al. ........... | 600/16 |
| 2007/0254593 A1 * | 11/2007 | Jollota et al. .............. | 455/67.11 |

* cited by examiner

*Primary Examiner*—Carl H Layno
*Assistant Examiner*—Jennifer Stewart
(74) *Attorney, Agent, or Firm*—Gael Diane Tisack; Mark L. Mollon; MacMillan, Sobanski & Todd (57) ABSTRACT

An artificial heart pump system has a heart pump implanted in a patient. A pump control unit worn by a patient includes a programmable device for adapting a secure aspect of heart pump operation in response to pump operating commands. The pump control unit has a wired interface and a wireless interface. A clinical external unit is adapted to be connected to the wired interface for delivering a pump operating command to the pump control unit. An auxiliary external unit is adapted to be connected to the wireless interface for collecting patient and/or pump system performance-related data from the pump control unit. The wireless interface is unable to consummate a pump operating command.

9 Claims, 11 Drawing Sheets

DUAL COMMUNICATION INTERFACE FOR ARTIFICIAL HEART SYSTEM

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to an artificial heart pump system, and, more specifically, to communication between a pump control unit worn by a patient and external units used by medical personnel to control heart pump operation and to collect patient and/or pump system performance-related data.

A heart pump system known as a left ventricular assist system (LVAS) is used for providing long term patient support with an implantable pump associated with an externally-worn pump control unit and batteries. The LVAS improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. The pump may be electronically controlled to provide a flow rate from two to eight liters per minute, for example. The desired flow rate depends on the size of the patient and the amount of assistance needed. The flow rate can also be varied in response to physiological changes of the patient.

An external unit (sometimes in the form of a hospital console), which is conventionally hard-wired to the externally-worn pump control unit, provides an interface for the health care professional to control the heart pump operation during setup and for subsequent adjustments. The external console unit also collects performance-related data from the pump control unit to verify 1) pump performance (e.g., the flow rate) and/or the condition of the patient. The monitored data may include pump conditions such as fault data that may be generated in the pump itself or patient conditions such as heart beat rate, blood pressure, or systemic resistance. The collected data is stored in the external console unit and can be analyzed by the health care professional to optimize the condition of the patient. The data may also be transferred by a hard-wired network connection from the external console unit to a centralized data management system for keeping track of status for a plurality of patients being cared for at a particular hospital ward, thereby allowing the health care professional to review the data for many patients at one convenient location.

Hard-wired communication provided by a cable between the pump control unit and the external console unit is desirable because of the security and reliability it provides. Interfering signals or misdirected control actions are not an issue for an isolated, hard-wired system. As another consequence, however, the patient must remain tethered to the external unit whenever communication is desired. Thus, times of patient mobility result in a lapse in the ability to monitor the pump operation.

SUMMARY OF THE INVENTION

As opposed to controlling pump operation, data monitoring does not require the same level of securing and reliability, so it would be acceptable to utilize wireless communication for data monitoring. By untethering the patient except during times that a secure aspect of heart pump operation needs to be adjusted, the patient's quality of life can be improved. Providing a wireless interface to the pump control unit, however, may lead to the risk that secure aspects of heart pump operation could be influenced over the wireless interface without the security and reliability of a wired interface.

The present invention achieves improvements over the prior art according to new apparatus and methods for an artificial heart pump system having a dual communication interface, i.e., both wired and wireless interfaces. New operating protocols improve the reliability of wireless data communication while avoiding any compromise in security.

In one aspect of the invention, an artificial heart pump system is provided in which a heart pump is implanted in a patient. A pump control unit worn by a patient includes a programmable device for adapting a secure aspect of heart pump operation in response to pump operating commands. The pump control unit has a wired interface and a wireless interface. A clinical external unit is adapted to be connected to the wired interface for delivering a pump operating command to the pump control unit. An auxiliary external unit is adapted to be connected to the wireless interface for collecting performance-related data (e.g., pump system data and/or patient data) from the pump control unit. The wireless interface is unable to consummate a pump operating command.

DETAILED DESCRIPTION OF PREFERRED EMBODIMENTS

According to the present invention, the external unit uses wired communication for secure aspects of heart pump operation such as pump configuration or parameter settings. In addition, if a communication event includes a large amount of data, such as a controller software update, the wired communication can provide a higher rate of data transfer than wireless. The external unit uses wireless communication for any other communications that don't require high security, such as data monitoring. The wireless communication allows patients to move freely and potentially to leave the hospital to go home while continuing to perform data monitoring. In that regard, a preferred embodiment of the invention employs two different kinds of external units, a clinical external unit having a wired interface to the pump control unit and an auxiliary external unit having a wireless interface to the pump control unit. The clinical external unit may additionally have a wireless interface so that tethering by a cable is only necessary during the hospital stay when adjusting a secure pump operation.

The software in a programmable device (e.g., microcontroller) contained in the pump control unit can distinguish any commands it receives according to the interface over which it was received. If a pump operation command is received from the wireless interface, it is rejected because that is the wrong interface for such commands.

With data monitoring being accomplished via a wireless interface, the external unit does not need to be located at the patient's bedside. It can be placed at a nurse's station or in a doctor's room for easier access. The external unit can also provide the capability to prepare data for a central data management system located in the hospital from where the data of multiple patients can be managed together. The external unit can also be connected to a communication network such as the telephone system or the Internet to send data from a patient's home to the central data management system automatically. By providing periodic transmission of performance-related data from the patient's home to the central data management system, the frequency of trips to the hospital can be reduced while improving system monitoring and patient care. Personnel and hospital costs are also reduced in connection with the treatment of ventricular-assist patients.

Figure 1:
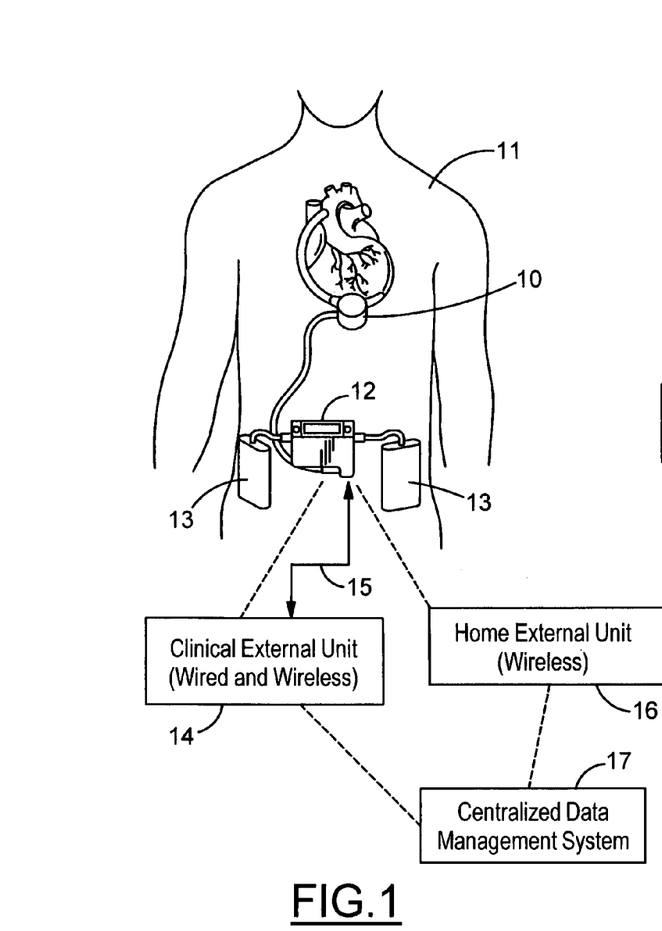
FIG. 1 illustrates an artificial heart pump system of the invention.

Referring now to FIG. 1, a blood pump 10 is implanted inside a human body 11 and connected to a pump control unit 12 worn by the patient. Power is supplied to pump control unit 12 from batteries 13 that are also worn by the patient. Pump control unit 12 may be connected to a clinical external unit 14 via a cable 15. Wireless communication may also take place between pump control unit 12 and clinical external unit 14. An auxiliary (e.g., home) external unit 16 has wireless communication with pump control unit 12 for data monitoring purposes. A centralized data management system 17 communicates with both clinical external unit 14 and auxiliary external unit 16 over any appropriate wired or wireless communication channel.

Figure 2:
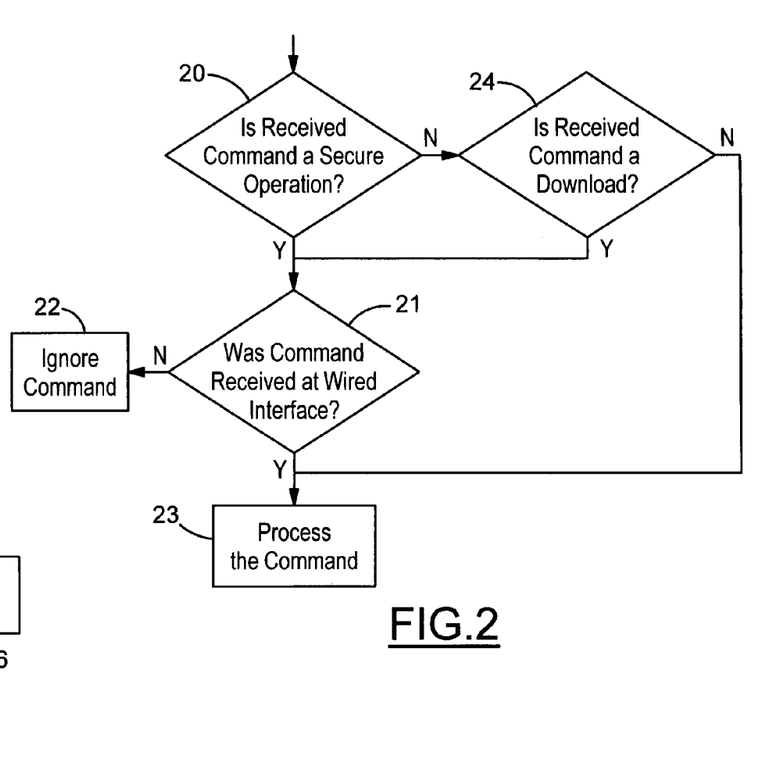
FIG. 2 is a flowchart of a method of the invention.

One overall method utilized by pump control unit 12 is shown in FIG. 2. When a command is received by the pump control unit, a check is made in step 20 to determine whether the received command corresponds to a secure operation of the pump. If it does, then a check is made at step 21 to determine whether the command was received over the wired interface. If not, then the command is ignored at step 22 and the wireless interface is, therefore, unable to consummate a pump operating command. If it is determined at step 21 that the command was received at the wired interface, then the command is processed at step 23. If the command received at step 20 is not a secure operation, then a check is made at step 24 to determine whether the received command corresponds to a download of information (e.g., updating of software). If it does, then the command is checked for having been received over the wired interface at step 21. If not a download command, then the command is permissible for the wireless interface and it is processed at step 23. As described in greater detail below, commands that may be sent wirelessly from an external unit to the pump control unit include requests for performance-related data and acknowledgements of previously received communications.

There are many alternative techniques for making the determination of whether a particular command has been received over the wired interface or the wireless interface. As described in greater detail below, there may be separate UART channels for receiving wired or wireless signals, thereby allowing the microcontroller to identify the source of an incoming command. Alternatively, a cable sensor can be incorporated in the cable connector on the pump control unit to generate a sensor signal to inform the microcontroller of the presence or absence of a cable. The microcontroller then disables commands for any secure pump operations when no cable is present.

Figure 3:
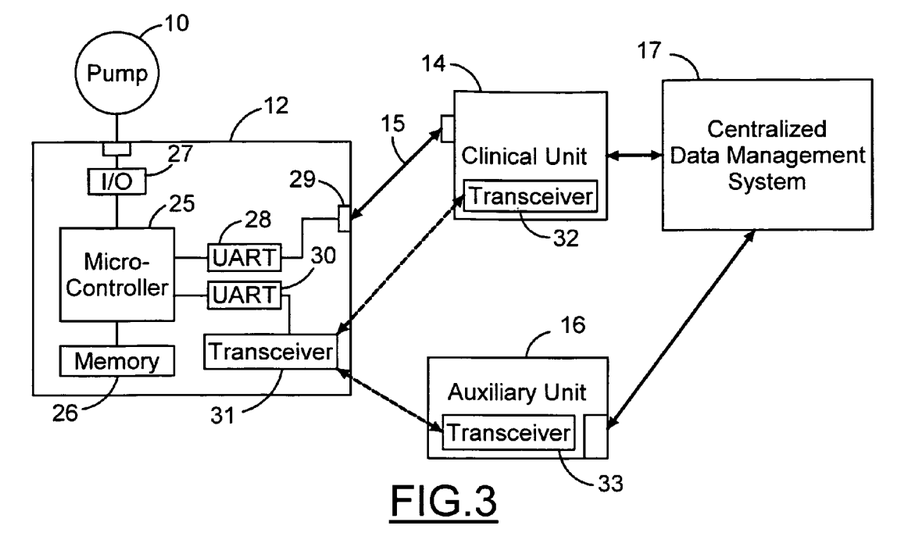
FIG. 3 is a block diagram of a first embodiment of the invention using two-way wireless communication.

The invention is shown in greater detail in FIG. 3. Pump control unit 12 includes a programmable device such as a microcontroller 25 having a memory 26 and connected to pump 10 by an input/output interface 27. A hardwired interface between microcontroller 25 and clinical unit 14 includes a UART 28 coupled between microcontroller 25 and a cable connector 29. Microcontroller 25 further has a wireless interface comprised of a UART 30 connected to a wireless transceiver 31. Transceiver 31 may utilize a known wireless protocol such as Bluetooth, for example. Compatible transceivers 32 and 33 are contained in clinical external unit 14 and auxiliary external unit 16. Units 14 and 16 are further connected to a centralized data management system 17 for optional collection and long term archival of data.

Figures 4, 7:
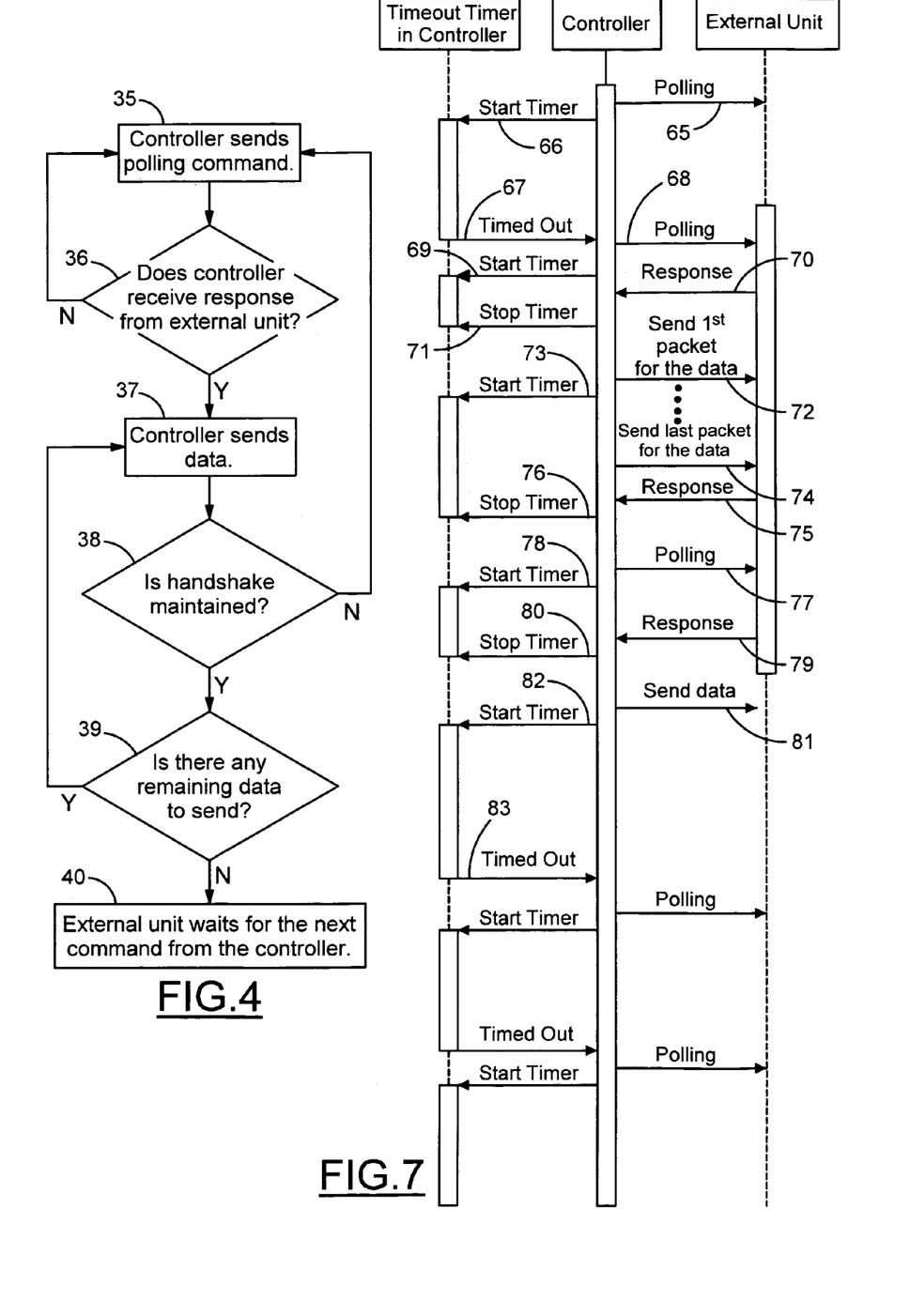
FIG. 4 is a flowchart showing one preferred method of system operation for the embodiment of FIG. 3.
FIG. 7 is a timing diagram showing an example timing sequence according to FIGS. 4-6.

An overall communication protocol for the system of FIG. 3 is shown in FIG. 4. The microcontroller preferably operates the wireless interface in two respective modes, a polling mode and a data transfer mode. In the polling mode, the controller sends a polling command over the wireless interface in step 35. If the external unit receives a polling command then it generates an acknowledgement or handshake response and sends it wirelessly back to the pump control unit. A check is made in step 36 to determine whether the microcontroller received a response from the external unit. If not, then the microcontroller remains in the polling mode and returns to the transmission of a polling command in step 35. If a response from the external unit is received, then the microcontroller enters the data transfer mode and sends data wirelessly in step 37. As the microcontroller sends data, a check is made in step 38 to determine whether a handshake is maintained with the external unit in step 38. If handshake is lost while data is being sent, then a return in made to step 35. If handshake is maintained, then a check is made in step 39 to determine whether the microcontroller has any remaining data to be sent. If so, then a return is made to step 37. Otherwise, the external unit merely waits for the next external command to be received from the controller in step 40.

Figures 5, 6:
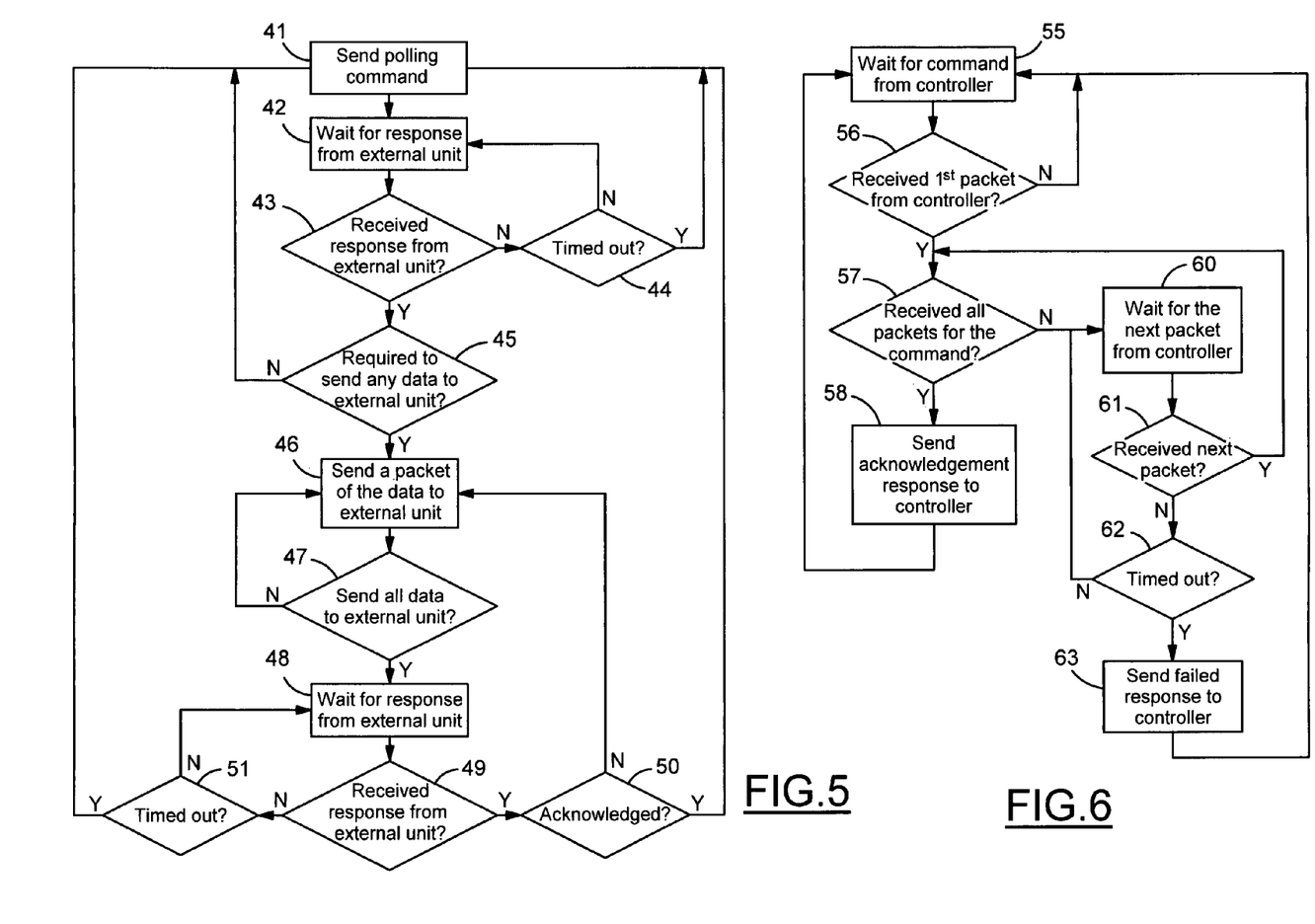
FIG. 5 is a flowchart of one preferred method for operating the pump control unit of FIG. 3.
FIG. 6 is a flowchart of one preferred method for operating the external unit of FIG. 3.

Operation within the pump control unit is shown in greater detail in FIG. 5. The polling command is sent in step 41. The microcontroller waits for a response from the external unit in step 42. A check is made in step 43 to determine whether a response was received from the external unit. If not, then a check is made in step 44 to determine whether the expected time for receiving a response has timed out. If not, then a return is made to step 42 to wait for a response. If timed out, then a return is made to step 41 to repeat the polling command. Once a response is received in step 43, a check is made in step 45 to determine whether any additional data is present in the pump control unit that should be sent to the external unit. If not, then a return is made to step 41 to send a polling command whenever additional data becomes available. Otherwise, a packet of data is sent to the external unit in step 46. A check is made in step 47 to determine whether all data packets have been sent. If not, then a return is made to step 46 for sending the additional data packet. Once all data is sent, the microcontroller waits for a response from the external unit in step 48. A check is made in step 49 to determine whether a response has been received from the external unit. If so, then a check is made in step 50 to determine whether correct reception of the data is acknowledged by the external unit. If not, then a return is made to step 46 to resend the data. If the response from the external unit acknowledges error-free reception, then a return is made to step 41 to re-initiate polling when another data transfer becomes necessary. If no response has been received from the external unit in step 49, then a check is made for a timed-out condition in step 51. If not timed out, then a return is made to step 48 to continue waiting for a response. If timed out, then return is made to step 41 to reinitiate the data transfer.

FIG. 6 shows the operation at the external unit in greater detail. The external unit waits for a command from the controller at step 55. Once a command is received, a check is performed in step 56 to determine whether a first data packet has been received from the controller. If not, then a return is made to step 55. Otherwise, a check is made in step 57 to determine whether all packets for a particular data transfer command had been received. If yes, then the external unit sends an acknowledgement response to the controller in step 58 and then returns to step 55 to wait for the next command. If all packets are not received in step 57, then the external unit waits for the next packet from the controller in step 60. It checks in step 61 to determine whether the next packet has been received. If so, then a return is made to step 57 to determine whether all packets have now been received. If not, then a check is made in step 62 to determine whether the expected delay has timed out. If not, then a return is made to step 60 to wait for the next packet. Otherwise, a timeout is detected and the external unit sends a response indicative of failure to the controller and then returns to step 55 for waiting for the next command.

FIG. 7 shows a timing diagram wherein various actions are given in a timing sequence moving from the top of FIG. 7 toward the bottom. Initially, the controller sends a polling command at an event 65. It then starts its timeout timer at an event 66. As shown by the dashed lines under the external unit, the polling command at event 65 is not received by the external unit (e.g., it is out of range) so that there is no response. The timeout timer expires at an event 67 causing the controller to initiate a new polling command at an event 68. The controller restarts the timeout timer at event 69, but this time a response is received from the external unit at an event 70 causing the controller to stop the timer at an event 71. Based on the response, the controller sends a packet of data to the external unit at an event 72. The timeout timer is again started at an event 73 while the controller continues to send packets of the data. A last packet is sent at an event 74 followed by an acknowledgement response from the external unit at event 75 causing the controller to stop the timeout timer at event 76.

When the controller again has data to be automatically sent to the external unit, it begins a new polling command at event 77. The polling timeout timer is started at event 78, and a response is received at event 79. The controller stops the timer at event 80 and then begins to send data at event 81. It starts the sending timeout timer at event 82, but the wireless link again fails between the controller and the external unit (e.g., they are moved out of range) resulting in a time out condition at an event 83. Thereafter, the controller periodically generates polling commands in an attempt to reestablish communication with the external unit.

Figure 8:
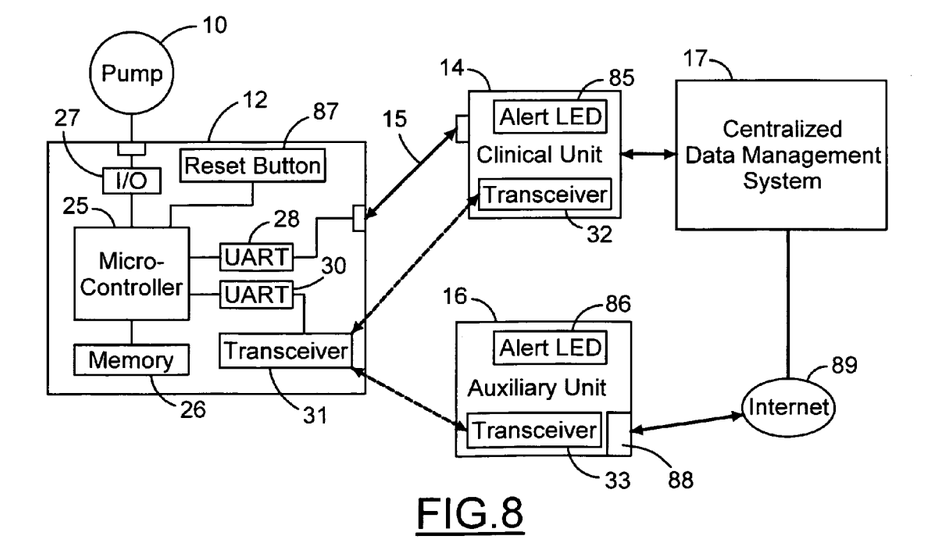
FIG. 8 is a block diagram of a second embodiment of the invention using two-way wireless communication.

An alternative embodiment employing two-way wireless communication between pump control unit 12 and external units 14 and/or 16 is shown in FIG. 8. In this embodiment, the polling mode employs two-way wireless communication while only one-way wireless communication is enabled during the data transfer mode. In other words, reception of a wireless acknowledgement signal from the external unit to the pump control unit is not allowed. Instead, user intervention provides the acknowledgement by virtue of an alert LED 85 on the clinical external unit 14 and an alert LED 86 on the auxiliary unit 16. The alert LEDs operate in conjunction with a reset button 87 that is provided on the pump control unit 12 in communication with microcontroller 25. Reset button 87 is a switch element that can be manually activated to initiate an input signal to microcontroller 25. Alert LEDs 85 and 86 can alternatively take the form of any visual indicator such as any optical display or light, or any audible indicator such as a beep from a speaker.

Auxiliary unit 16 as shown in FIG. 8 may preferably be a home data unit taken with the patient while away from the hospital. In order to transfer collected performance-related data to centralized data management system 17, auxiliary unit 16 includes a modem 88 (which may be a dial up modem or a cable modem, for example) to communicate with internet 89 for transferring data to system 17.

Figure 9:
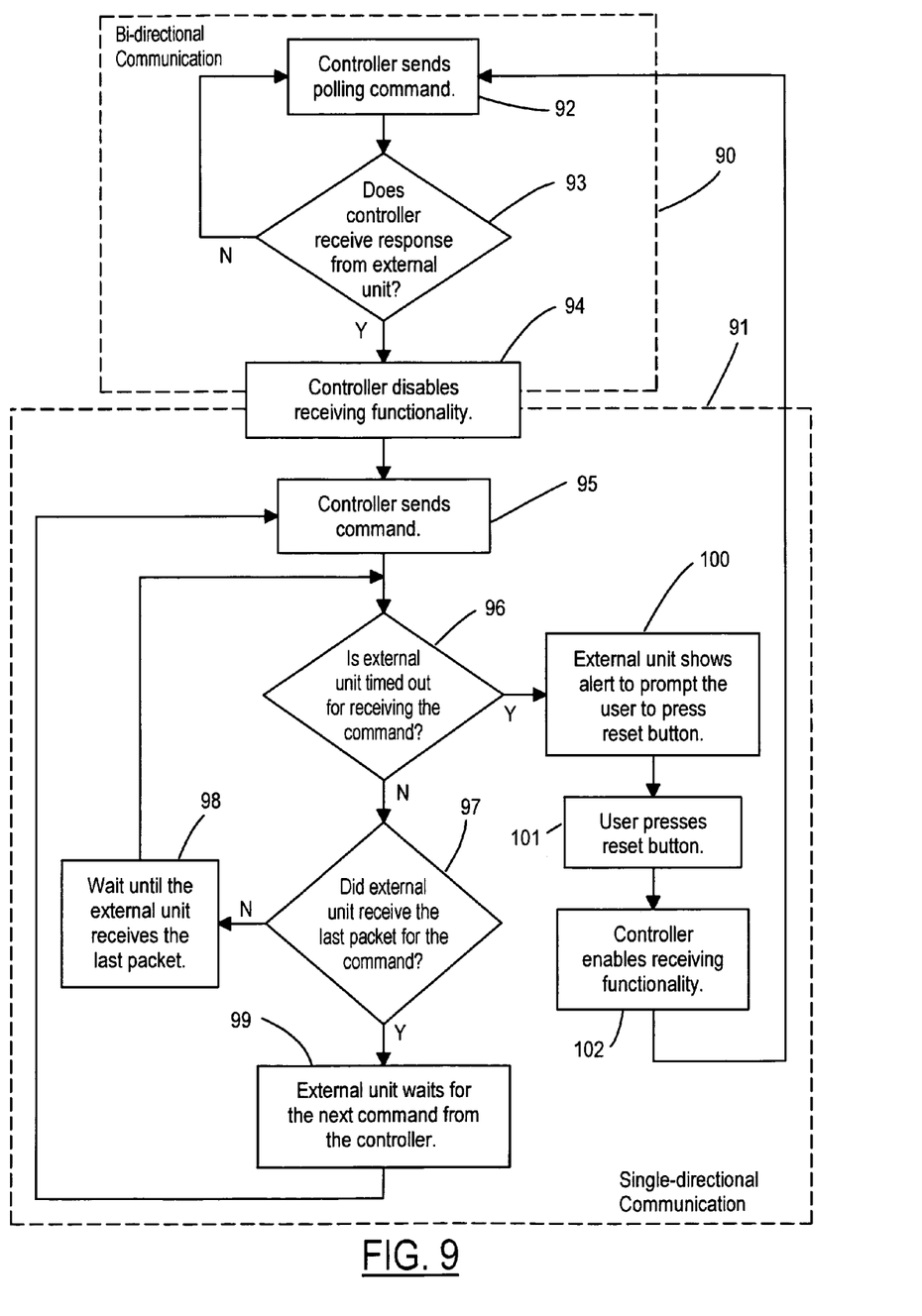
FIG. 9 is a flowchart showing one preferred method of system operation for the embodiment of FIG. 8.

A preferred communication protocol for the system of FIG. 8 is shown in FIG. 9 including a bi-directional communication portion 90 and a single-directional communication portion 91. The pump controller begins in a bi-directional communication state and sends a polling command in step 92. A check is made in step 93 to determine whether the controller receives a wireless acknowledgement response from the external unit. Once a response is received, the controller disables its receiving functionality in step 94 and enters a single-directional communication state.

The controller sends a data command reporting the performance-related data in step 95. At step 96, the external unit checks to determine whether a predetermined period of time has timed out without receiving a command from the controller since the external unit responded to the polling command. If not, then the external unit checks in step 97 to determine whether it received a last data packet. If not, then it waits for the next packet in step 98. After receiving the last packet, the external unit waits for the next command from the controller in step 99.

If the external unit times out at step 96, then it generates an alert indication in step 100 (e.g., by turning on an alert LED or by generating an audible beep) to prompt the user to press the reset button. The user presses the reset button in step 101, causing the controller to re-enable its receiving functionality in step 102 and then return to the sending of a polling command in step 92.

Figure 10:
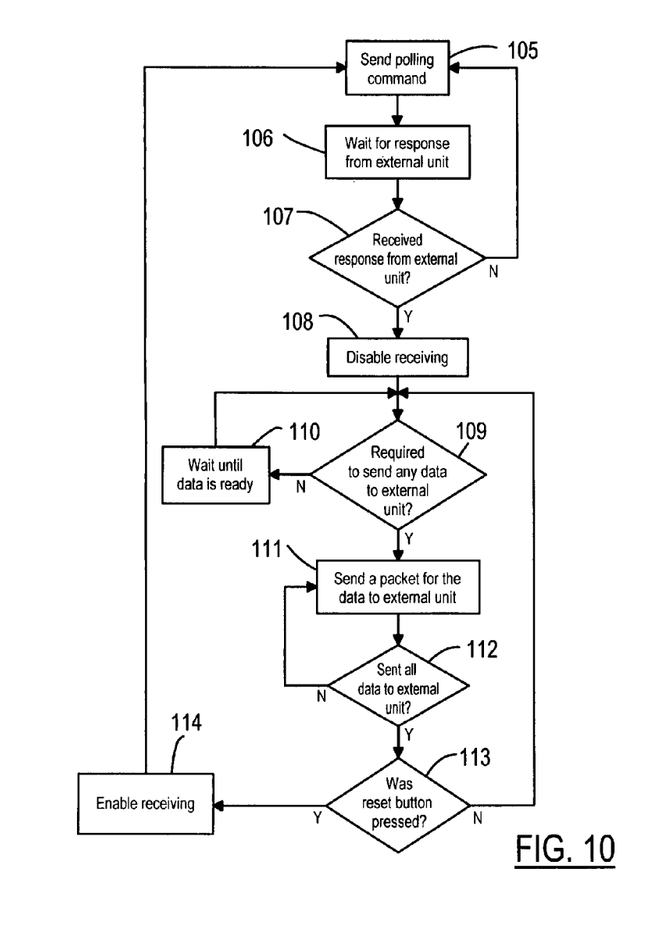
FIG. 10 is a flowchart of one preferred method for operating the pump control unit of FIG. 8.

FIG. 10 shows a preferred operating method of the pump control unit for the embodiment of FIGS. 8 and 9. The controller sends the polling command in step 105 and waits for a response from the external unit in step 106. A check is made in step 107 to determine whether a response is received from the external unit. If not, then another polling command is sent in step 105. If the acknowledgement was received, then the receiving function of the pump control unit is disabled in step 108. The controller checks in step 109 to determine whether there is any required data to be sent to the external unit. If not, then it waits until the data is ready in step 110. When data is ready, then the controller sends a packet of the data to the external unit in step 111. It checks in step 112 to determine whether all data has been sent and continues sending in step 111 until all data is sent. A check is made in step 113 to determine whether the reset button has been pressed. If not, then the controller continues sending data as it becomes available at step 109. When the reset button is pressed, the controller enables receiving at step 114 and returns to step 105 to send a polling command.

Figure 11:
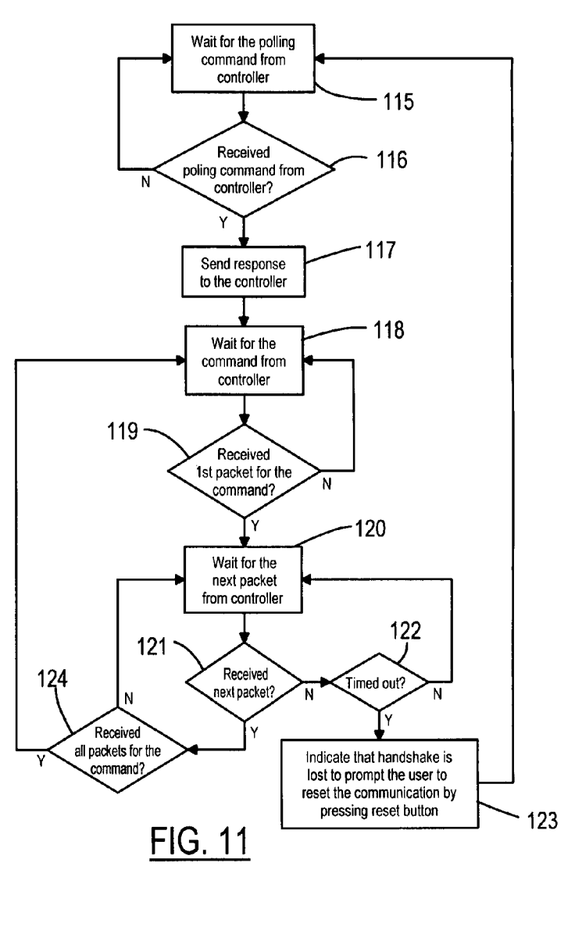
FIG. 11 is a flowchart of one preferred method for operating the external unit of FIG. 8.

FIG. 11 shows a preferred operating method of the external unit according to the embodiment of FIGS. 8 and 9. The external unit waits for a polling command in step 115. Step 116 determines whether a polling command has been received. Once a polling command is detected, the external unit sends a response to the controller in step 117. The external unit waits for a data command in step 118 and checks in step 119 to determine whether a first packet for the command has been received. After receiving the first packet, the external unit waits for the next packet in step 120. If a next packet is not detected in step 121, then a check is made in step 122 to determine if a predetermined time period has timed out. If not, then the external unit continues to wait for the next packet in step 120. If timed out in step 122, then the external unit activates the indicator to indicate that handshake has been lost with the pump control unit so that the user will be prompted to reset the communication by pressing the reset button. Then the external unit waits for a polling command in step 115. If a next packet is received in step 121, then a check is made in step 124 to is determine whether all packets for the command have been received. If not, then the external unit returns to step 120 to wait for the next packet. Once all packets are received, then a return is made to step 118 to wait for the next command.

Figure 12:
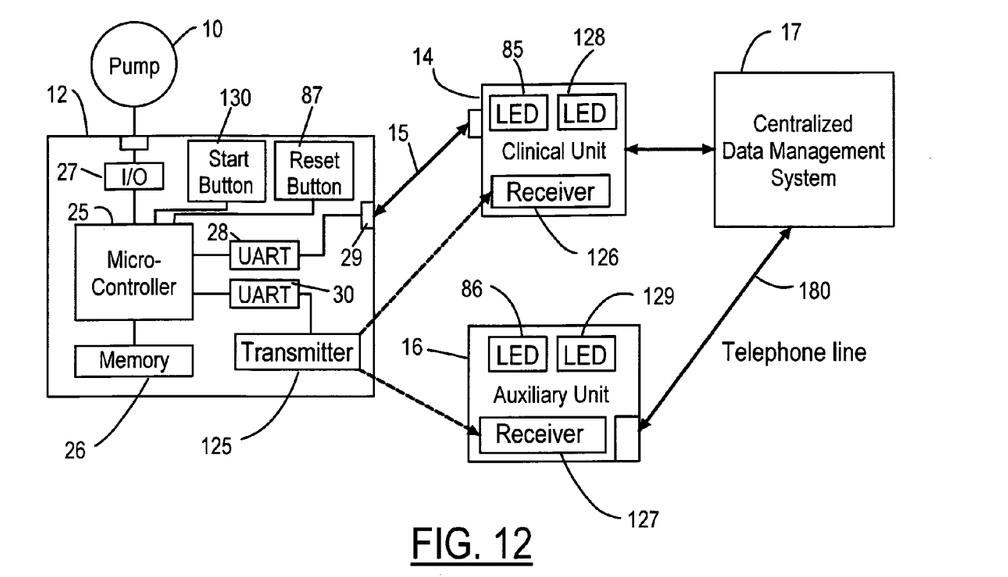
FIG. 12 is a block diagram of a third embodiment of the invention using one-way wireless communication.

FIG. 12 shows an embodiment of the invention employing only one-way wireless communication from pump control unit 12 to external units 14 and/or 16. Thus, pump control unit 12 includes a transmitter 125 instead of a transceiver and external units 14 and 16 have receivers 126 and 127, respectively. In addition to alert indicators 85 and 86, external units 14 and 16 include acknowledgement indicators 128 and 129. In addition to reset button 87, pump control unit 12 includes a start button 130 connected to microcontroller 25. In this embodiment, no wireless commands can be sent from the external units to the pump control unit. Therefore, the pump control unit cannot obtain an automatic wireless response to its polling command. Instead, manual intervention (e.g., by the patient) is utilized as follows.

Figure 13:
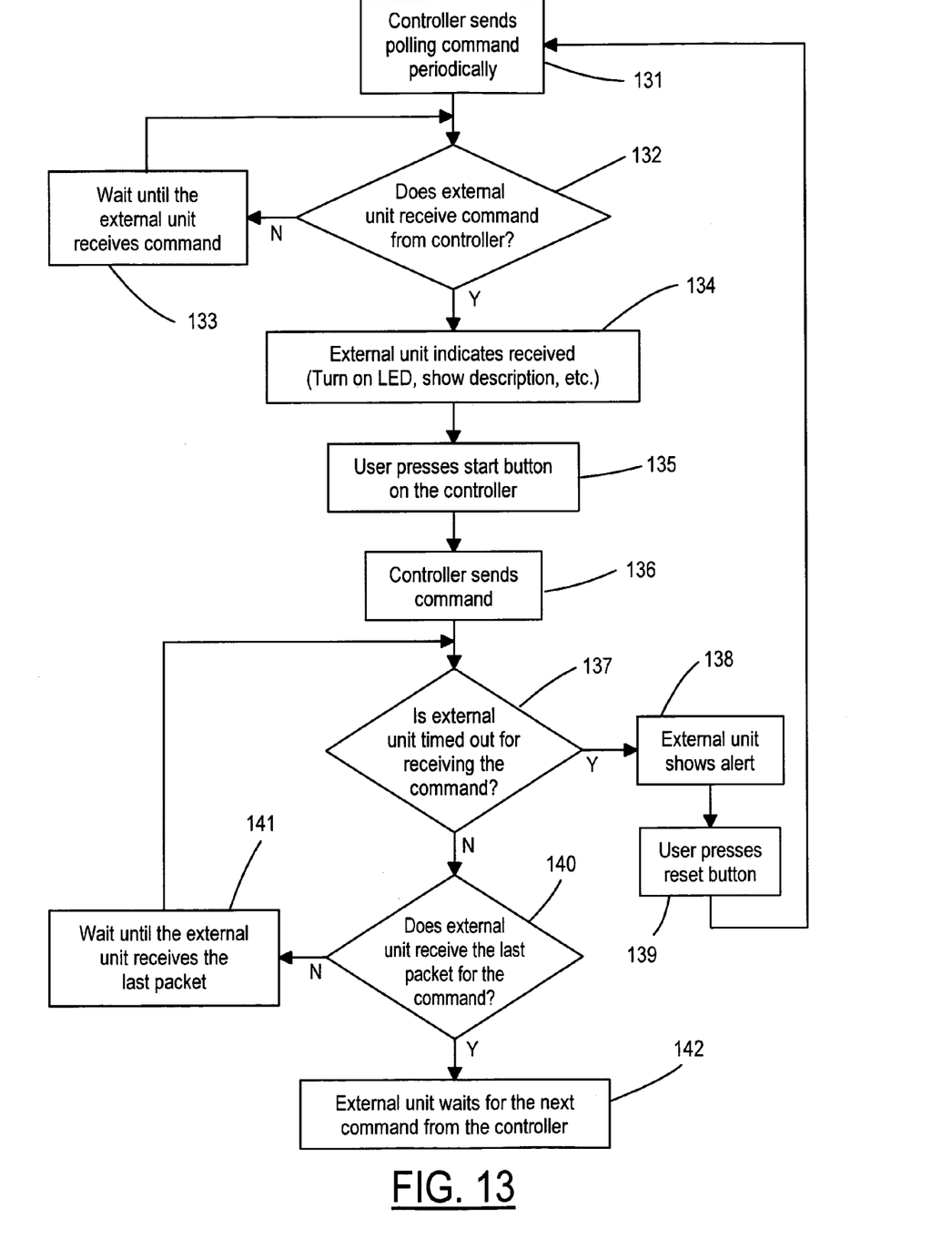
FIG. 13 is a flowchart showing one preferred method of system operation for the embodiment of FIG. 12.

FIG. 13 shows the overall communication protocol for FIG. 12. In step 131 the controller sends a polling command on a periodic basis (e.g., once per minute). In step 132, the external unit continuously checks to determine whether it has received a polling command from the controller. If not, then it waits for such a command in step 133. When a polling command is received by the external unit, it indicates this in step 134 by generating an acknowledgement indication (turning on the LED, generating a message on a display, creating an audible sound, or any other perceivable signal). In response to the acknowledgement indication, the user presses the start button on the pump control unit in step 135. The microcontroller detects the signal from the start button and then initiates wireless transmission of a data command in step 136. While the controller is sending data commands, the external unit checks for a timed out condition in step 137. If the external unit has timed out for receiving a command, then it shows in alert indication in step 138. When the user sees the alert signal, the user presses the reset button in step 139 causing the controller to return to its polling command in step 131. When the external unit is not timed out for receiving a command in step 137, it determines in step 140 whether it has received the last packet for the command. If not, then it waits for the last packet in step 141. When the last command is received, the external unit waits for the next command from the controller in step 142.

Figure 14:
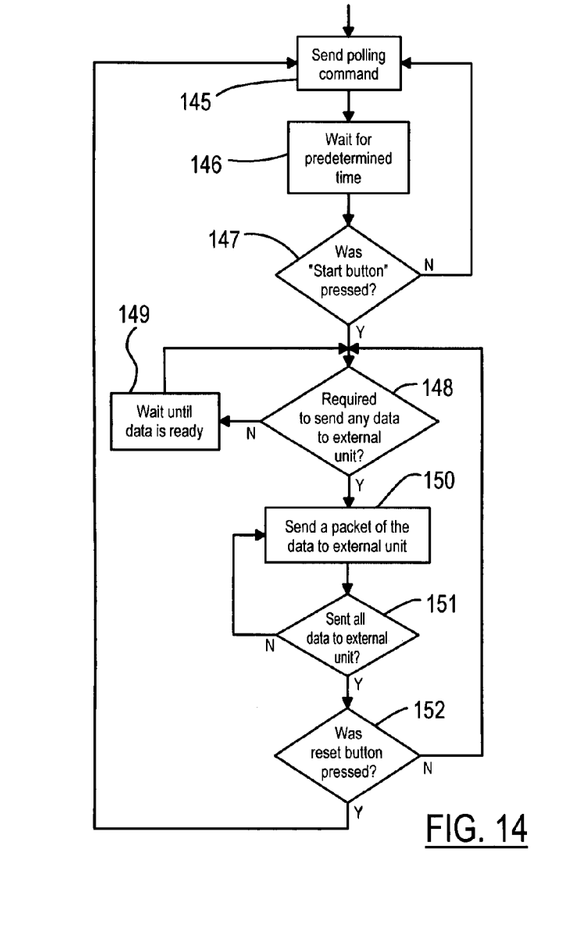
FIG. 14 is a flowchart of one preferred method for operating the pump control unit of FIG. 12.

Operation of the pump control unit is shown in greater detail in FIG. 14. It sends a polling command in step 145 and then waits a predetermined time in step 146 until it checks in step 147 to determine whether the start button was pressed. Once it determines that the start button was pressed, the pump control unit sends any required data in step 148. It continues to send data in steps 150 and 151 until all data has been sent. The pump control unit checks whether the reset button was pressed in step 152. If not, then data continues to be sent. However, once the reset button is pressed in step 152, then the pump control unit immediately returns to step 145 to send a polling command.

Figure 15:
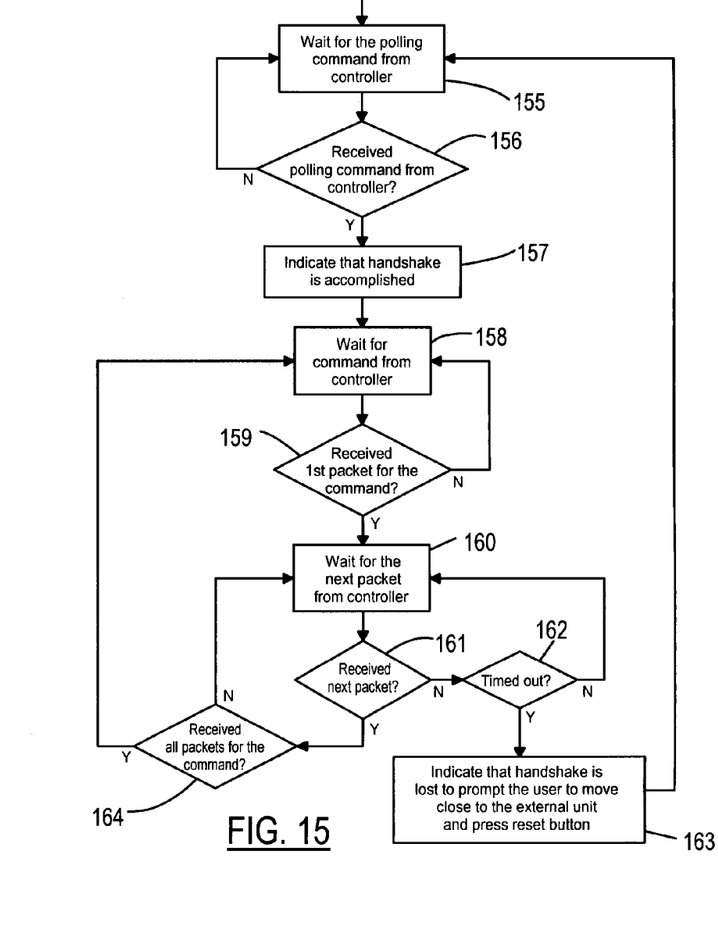
FIG. 15 is a flowchart of one preferred method for operating the external unit of FIG. 12.

FIG. 15 shows the operation of the external unit in greater detail. It waits for reception of a polling command in steps 155 and 156. In step 157, the external unit turns on the acknowledgement indicator to show that a handshake should be initiated with the pump control unit by means of the user pressing the start button. The external unit waits for a command from the controller in step 158 and checks for reception of a first data packet in step 159. After receiving a first packet, the external unit waits for next data packets in step 160 while detecting reception or timing out of the next packets in step 161 and 162. If a time out is detected in step 162 because of an incomplete transmission, then the alert indicator is turned on in step 163 to indicate that handshake is lost so that the user is prompted to move closer to the external unit and then wait for an acknowledgement indication. Step 164 determines whether all packets are received and then returns to step 158 for a next command.

Figure 16:
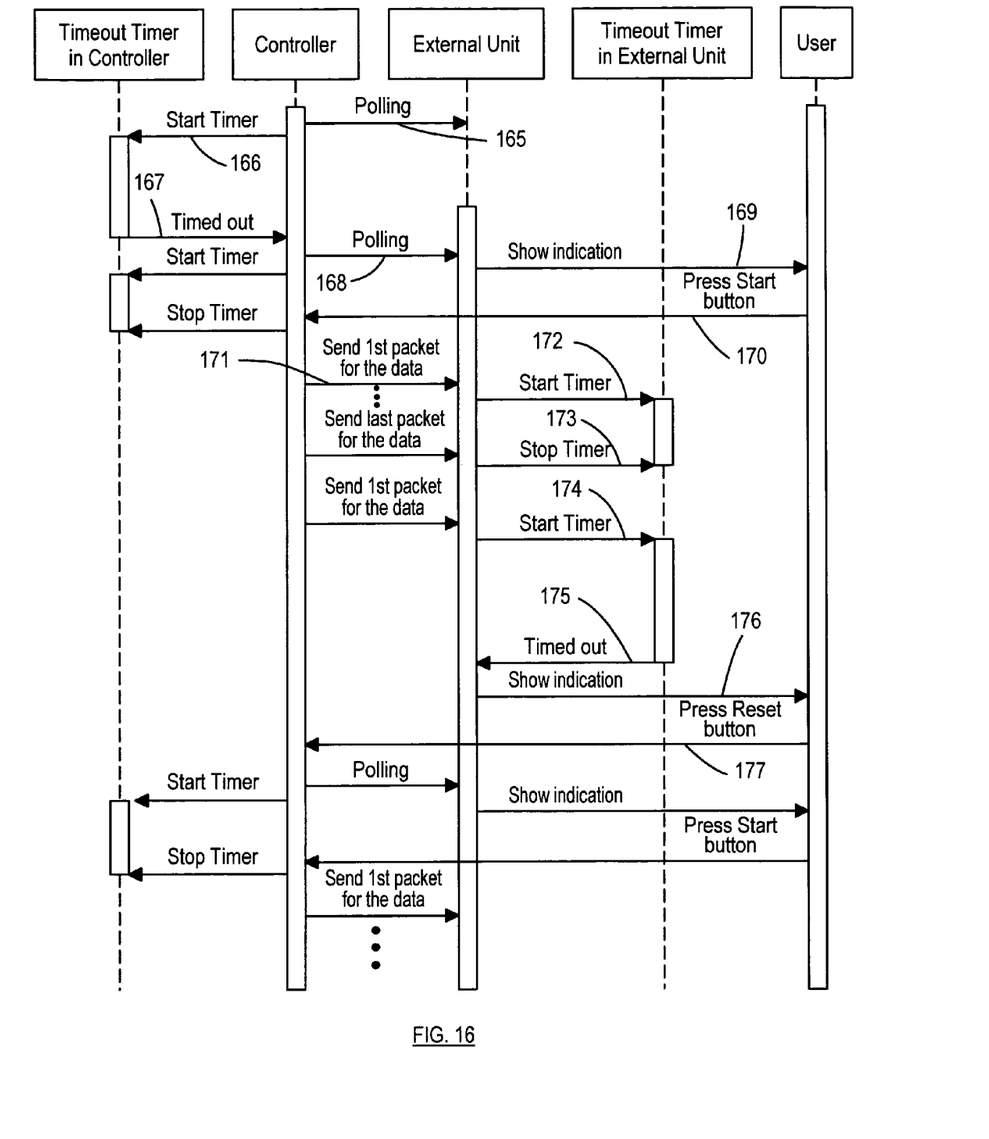
FIG. 16 is a timing diagram showing an example timing sequence according to FIGS. 13-15.

FIG. 16 is a timing diagram corresponding to the embodiment of FIGS. 12-15. The controller sends a polling command at an event 165 and starts the timer at event 166. The external unit does not receive the initial polling command and so the time-out timer reaches a timed-out condition at event 167. The controller sends a new polling command at event 168 which is received by the external unit, thereby causing is the external unit to show an acknowledgement indication at an event 169. The indication is seen by the user who presses the start button at an event 170. The controller begins sending data packets at an event 171. As the external unit waits for data packets from the controller, it starts and stops its own time out timer at events 172-174. At event 175, the time-out timer in the external unit has expired without receiving a last packet of data. As a result, the external unit shows an alert indication at an event 176 to show that there was an incomplete transmission. The user sees the alert indication and presses the reset button at an event 177. In response to the signal from the reset button, the controller reinitiates a sequence involving the reception of the polling command by the external unit, pressing of the start button by the user, and resumption of transmission of data packets.

Figure 17:
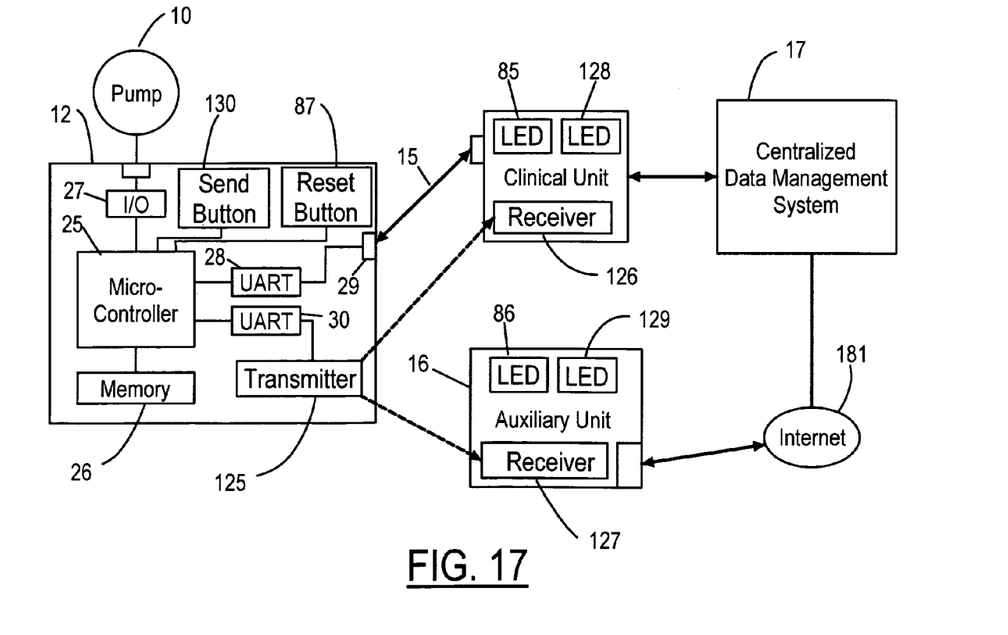
FIGS. 17 and 18 are block diagrams showing alternative embodiments for the backend communication to the centralized data management system.
Figure 18:
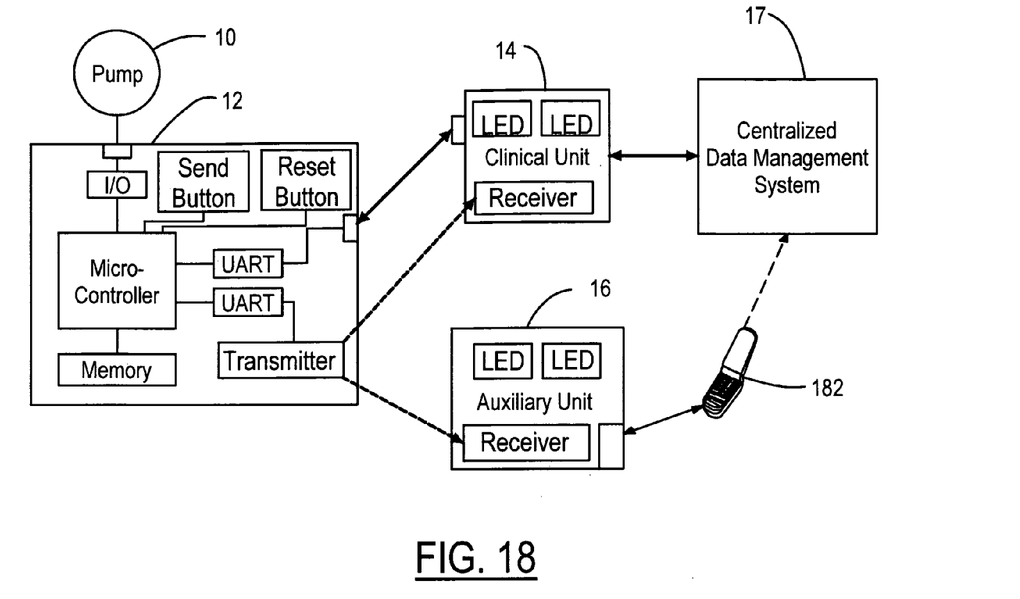

Returning to FIG. 12, a telephone line 180 is shown for interconnecting auxiliary unit 16 and centralized data management system 17. Alternatively, an Internet connection 181 can be used as shown in FIG. 17. In yet another alternative, a cellular network connection 182 can be employed as shown in FIG. 18 as part of a data link between auxiliary unit 16 and data management system 17. In each embodiment, the auxiliary unit periodically establishes a communication link to the data management system in order to provide updated data that has been collected from the pump control unit.

Figure 19:
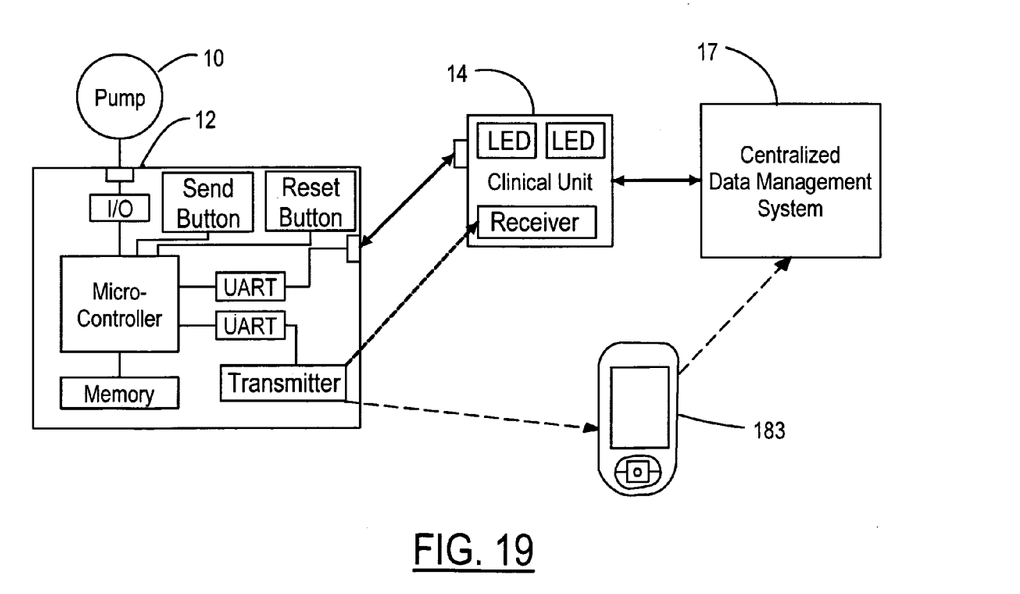
FIG. 19 is a block diagram showing an alternative embodiment using a smart phone device for the auxiliary unit.

FIG. 19 shows another embodiment employing a smart phone 183 for implementing the auxiliary unit together with the communication link to data management system 17. Thus, an appropriate software application is provided for smart phone 183 allowing it to communicate wirelessly with pump control unit 12 to obtain patient and performance-related data and to periodically transmit the data to the data management system.

What is claimed is:

1. An artificial heart pump system in which a heart pump is implanted in a patient, comprising:
  a pump control unit to be worn by a patient including a programmable device for adapting a secure aspect of heart pump operation in response to pump operating commands, wherein the pump control unit has a wired interface and a wireless interface;
  a clinical external unit adapted to be connected to the wired interface for delivering a pump operating command to the pump control unit; and
  an auxiliary external unit adapted to be connected to the wireless interface for collecting performance-related data from the pump control unit, wherein the wireless interface is unable to consummate a pump operating command;
  wherein the wireless interface is two-way, wherein the pump control unit further includes a first transceiver, wherein at least one of the external units includes a second transceiver, wherein the programmable device determines presence of the at least one external unit by operating the wireless interface in a polling mode, wherein the programmable device operates the wireless interface in a data transfer mode in response to detecting presence of the at least one external unit, wherein the programmable device disables the receiving functionality of the first transceiver during the data transfer mode, and wherein the programmable device automatically sends the performance-related data over the wireless interface when in the data transfer mode; and
  wherein the at least one external unit detects an incomplete transmission of performance-related data, wherein the at least one external unit includes an alerting indicator for indicating the occurrence of the incomplete transmission, wherein the pump control unit includes a reset element for being manually activated in response to the indication by the alerting indicator, and wherein the programmable device returns the wireless interface to the polling mode in response to the manual activation.

2. The system of claim 1 further comprising:
  a centralized data management system in communication with at least one of the external units for receiving performance-related data for analysis by a health care professional.

3. The system of claim 2 wherein the clinical external unit is connected to the wireless interface for collecting the performance-related data, and wherein the centralized data management system is further in communication with a plurality of other wireless interfaces for other pump control units in a health care facility.

4. The system of claim 2 wherein the auxiliary external unit is remotely located from the centralized data management system, and wherein the auxiliary unit is in communication with the centralized data management system via a data network connection for transmitting the performance-related data.

5. The system of claim 2 wherein the auxiliary external unit is remotely located from the centralized data management system, and wherein the auxiliary unit is in communication with the centralized data management system via a telephone network connection for transmitting the performance-related data.

6. The system of claim 2 wherein the auxiliary external unit is remotely located from the centralized data management system, and wherein the auxiliary unit is comprised of a smart phone device in communication with the centralized data management system via a wireless cellular network connection for transmitting the performance-related data.

7. An artificial heart pump system in which a heart pump is implanted in a patient, comprising:
  a pump control unit to be worn by a patient including a programmable device for adapting a secure aspect of heart pump operation in response to pump operating commands, wherein the pump control unit has a wired interface and a wireless interface;
  a clinical external unit adapted to be connected to the wired interface for delivering a pump operating command to the pump control unit; and
  an auxiliary external unit adapted to be connected to the wireless interface for collecting performance-related data from the pump control unit, wherein the wireless interface is unable to consummate a pump operating command;
  wherein the pump control unit further includes a one-way transmitter for the wireless interface operable in a polling mode or a data transfer mode, wherein at least one of the external units includes a receiver and an acknowledgement indicator to indicate detection by the receiver of the polling mode, wherein the programmable device initiates operation of the wireless interface in the polling mode, wherein the pump control unit includes a start element coupled to the programmable device for being manually activated in response to the indication by the acknowledgement indicator, and wherein the programmable device operates the wireless interface in the data transfer mode in response to the manual activation of the start element; and
  wherein the at least one external unit detects an incomplete transmission of performance-related data, wherein the at least one external unit includes an alerting indicator for indicating the occurrence of the incomplete transmission, wherein the pump control unit includes a reset element for being manually activated in response to the indication by the alerting indicator, and wherein the programmable device returns the wireless interface to the polling mode in response to the manual activation.

8. A method of operating an artificial heart pump system in which a heart pump is implanted in a patient, comprising the steps of:

provide pump operating commands to a pump control unit to be worn by a patient, wherein the pump control unit includes a programmable device for adapting a secure aspect of heart pump operation in response to the pump operating commands, wherein the pump control unit has a wired interface for receiving the pump operating commands from a clinical external unit, and wherein the pump control unit has a two-way wireless interface including a first transceiver;

the programmable device collecting performance-related data in response to the heart pump operation;

operating the wireless interface of the pump control unit in a polling mode to determine presence of either the clinical external unit or an auxiliary external unit having a second transceiver that responds to the polling mode;

operating the wireless interface of the pump control unit in a data transfer mode in response to detection of one of the external units to automatically send the performance related data, wherein the data transfer mode includes disabling the receiving functionality of the first transceiver;

detecting an incomplete transmission of performance-related data;

indicating the occurrence of the incomplete transmission by activating an alerting element of the one external unit;

manually activating a reset element of the pump control unit in response to the indication by the alerting element; and returning the wireless interface to the polling mode in response to the manual activation.

9. The method of claim 8 further comprising the step of:

transmitting performance-related data from the detected external unit to a centralized data management system for analysis by a health care professional to determine the pump operating commands.

* * * * *